United States Patent
Bohlander et al.

(10) Patent No.: US 6,331,607 B1
(45) Date of Patent: Dec. 18, 2001

(54) METHOD FOR PRODUCING GLUCOPROTAMINES

(75) Inventors: Ralf Bohlander; Sven Jaensch, both of Duesseldorf; Dirk Springer, Haan, all of (DE)

(73) Assignee: Cognis Deutschland GmbH, Duesseldorf (DE)

( * ) Notice: Subject to any disclaimer, the term of this patent is extended or adjusted under 35 U.S.C. 154(b) by 0 days.

(21) Appl. No.: 09/508,929

(22) PCT Filed: Sep. 10, 1998

(86) PCT No.: PCT/EP98/05774

§ 371 Date: Jun. 8, 2000

§ 102(e) Date: Jun. 8, 2000

(87) PCT Pub. No.: WO99/15496

PCT Pub. Date: Apr. 1, 1999

(30) Foreign Application Priority Data

Sep. 19, 1997 (DE) .............................................. 197 41 356

(51) Int. Cl.[7] ............................. C08G 69/08; C08G 73/10
(52) U.S. Cl. ........................ 528/312; 528/310; 528/320; 528/328
(58) Field of Search .................................. 528/320, 310, 528/312, 328

(56) References Cited

U.S. PATENT DOCUMENTS

| | | | |
|---|---|---|---|
| 3,702,313 | * 11/1972 | Gilch et al. | 528/320 |
| 3,770,807 | * 11/1973 | Sumikawa et al. | 45/105.945 |
| 4,584,125 | * 4/1986 | Griswold et al. | 252/358 |
| 4,652,585 | * 3/1987 | Gerhardt et al. | 514/563 |
| 4,652,858 | * 3/1987 | Kokubo et al. | 340/347 |
| 5,352,756 | * 10/1994 | Meldal | 528/320 |
| 5,824,708 | * 10/1998 | Disch et al. | 514/563 |

FOREIGN PATENT DOCUMENTS

| | | | |
|---|---|---|---|
| 1 254 635 | * 11/1967 | (DE) | . |
| 1 493 991 | * 10/1969 | (DE) | . |
| 21 58 562 B2 | * 6/1972 | (DE) | . |
| 34 10 956 A1 | * 9/1985 | (DE) | . |
| 39 30 410 A | * 3/1991 | (DE) | . |
| 43 40 124 A1 | * 6/1995 | (DE) | . |
| 0 156 275 A2 | * 10/1985 | (EP) | . |
| 1 351 793 B | * 12/1963 | (FR) | . |

OTHER PUBLICATIONS

K. Disch, "Glucoprotamin—a New Antimicrobial Substance[1]", Hyg. Med., 17, No. 12, (1992), pp. 529–534.*

* cited by examiner

*Primary Examiner*—P. Hampton Hightower
(74) *Attorney, Agent, or Firm*—John E. Drach; Aaron R. Ettelman

(57) ABSTRACT

A process for producing glucoprotamines by condensation of N-substituted propylene diamines with 2-aminoglutaric compounds in which the reaction is carried out in the presence of aminosilicones is disclosed. Glucoprotamines produced in accordance with the disclosed process exhibit improved color quality and longer storage stability.

21 Claims, No Drawings

METHOD FOR PRODUCING GLUCOPROTAMINES

BACKGROUND OF THE INVENTION

Antimicrobial agents obtained by reacting N-substituted propylenediamines with 2-aminoglutaric acid esters are known from DE-A1 3410956 (Henkel). The amides formed in this reaction, which are marketed as Glucoprotamin®, may optionally be derivatized with alkylene oxides and/or acids. An overview of the antimicrobial properties of these substances was published in Hyg. Med. 17, 529 (1992). In addition, the use of Glucoprotamin® as a virucidal agent is known from DE-A1 4340124 (Ecolab).

Unfortunately, the known aminoglutaric acid ester amides have the disadvantage that concentrates, i.e. aqueous preparations thereof with an active substance content of about 20 to 50% by weight, are often neither color-stable nor storage-stable. On the contrary, the concentrates tend to thicken in storage, to separate crystals and to turn cloudy.

Accordingly, the complex problem addressed by the present invention was to provide a simple process by which glucoprotamines with excellent color quality, which would combine a low viscosity after dilution with water with improved storage stability, could be obtained in a high yield and selectivity.

BRIEF SUMMARY OF THE INVENTION

The present invention includes a process for the production of antimicrobial agents of the glucoprotamine type using aminosilicones and to their use as antifoam agents glucoprotamines by condensation of N-substituted propylene-diamines with 2-aminoglutaric compounds, characterized in that the reaction is carried out in the presence of aminosilicones.

It has surprisingly been found that the presence of aminosilicones not only reduces foaming during the condensation reaction, which is desirable from the point of view of process technology, it also leads to an increase in the volume/time yield. Through the inhibition of foaming, the elimination of water can be very closely controlled so that the exact degree of condensation required can be obtained.

In addition, it had not been expected that this measure would also lead to products distinguished by a much lighter color and distinctly improved stability in storage in relation to the prior art.

DETAILED DESCRIPTION OF THE INVENTION

N-substituted Propylenediamines

The N-substituted propylenediamnes to be used as starting materials preferably correspond to formula (I):

$$R^1\text{-NH-CH}_2\text{CH}_2\text{CH}_2\text{NH}_2 \quad (I)$$

in which $R_1$ is a linear alkyl group containing 6 to 22 carbon atoms and, more particularly, 12 to 14 carbon atoms. They may be obtained by the conventional methods of organic synthesis, for example by reaction of the corresponding alkylamines with acrylonitrile and subsequent hydrogenation [cf. for example FR-B 1351793]. N-substituted propylenediamines where the alkyl group contains 12 to 14 carbon atoms, the $C_{12}$ component preferably making up from 65 to 70 mole-%, have proved successful from the applicational point of view.

2-Aminoglutaric Derivatives

The 2-aminoglutaric derivatives suitable for use as the second component preferably correspond to formula (II):

in which $R^2$ is hydrogen or a $C_{1-4}$ alkyl group. Processes for their production are described, for example, in DE-AS 2158562, DE-OS 1493991 and DE-AS 1254635. D- or L-glutamic acid or racemates thereof are normally used, the L form preferably being used. Instead of the acid, its methyl, ethyl, propyl or butyl ester may also be used. If free glutamic acid is used, the condensation reaction may be carried out in the absence of a solvent and the water formed during the reaction may be directly distilled off.

Condensation Reaction

The condensation reaction is carried out in known manner, i.e. the N-substituted propylenediamnes and the 2-aminoglutaric derivatives are normally used in a molar ratio of 1:1 to 1:2. It is generally carried out at temperatures of 60 to 175° C. and is preferably carried out at temperatures in the range from 100 to 150° C.

Aminosilicones

The aminosilicones to be used in accordance with the invention are commercially available substances. Polymers containing 50 to 2,000, preferably 100 to 1,000 and more preferably 200 to 800 monomer units corresponding to formulae (IIIa) and (IIIb):

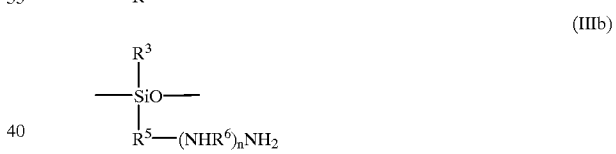

in which $R^3$ and $R^4$ independently of one another represent alkyl groups containing 1 to 8 carbon atoms, $R^5$ and $R^6$ independently of one another represent optionally hydroxysubstituted alkylene groups containing 1 to 8 carbon atoms and n is 0 or a number of 1 to 3, are preferably used. Aminosilicones corresponding to formula (III) which have a nitrogen content of 0.1 to 5 and more particularly 0.5 to 2% by weight are particularly preferred. These silicone compounds may be produced, for example, by equilibration of organopolysiloxanes and aminofunctional silanes or siloxanes, as described in U.S. Pat. No. 4,584,125. Suitable organopolysiloxanes are, for example, hexamethyl cyclotrisiloxane, octamethyl cyclotrisiloxane, trimethylsiloxy-terminated dimethyl or diethyl polysiloxanes. Examples of suitable aminofunctional siloxanes are γ-aminopropyl trimethoxysilane, γ-aminopropyl triethoxysilane and N-(β-aminoethyl)γ-aminopropyl trimethoxysilane. The aminosilicones are normally used in quantities of 0.0001 to 0.2, preferably 0.001 to 0.1 and more preferably 0.01 to 0.05% by weight, based on the glucoprotamine. Another advantage of the process according to the invention is that there is no need to use organic entraining agents to remove water, as described in EP-B1 0156275, so that the outlay on equipment involved in production is significantly reduced.

Commercial Applications

The glucoprotamines obtainable by the process according to the invention are far lighter in color than the prior art products so that colorless application solutions can be prepared for the first time. In contrast to the hitherto known processes, the presence of aminosilicones during the production process makes it possible to obtain even more concentrated active-substance solutions which have distinctly improved stability in storage and a lower viscosity due to the absence of unwanted polymers which can easily flocculate. Accordingly, the present invention also relates to the use of aminosilicones as antifoam agents and stabilizers in the condensation of N-substituted propylenediamnes with 2-aminoglutaric derivatives.

EXAMPLES

Comparison Example C1

501.8 g (2 moles) of a mixture of 70 mole-% dodecyl- and 30 mole-% tetradecyl propylenediamine and 322.2 g (2 moles) of L-glutamic acid-5-methyl ester were heated with stirring under nitrogen for 6 h to a maximum temperature of 133° C. (bottom), the methanol formed at 95 to 100° C. (bottom) being distilled off. On completion of the reaction, methanol residues were removed from the reaction mixture by brief application of a light vacuum (150 to 50 mbar) and stirring. 735.8 g (97% of theoretical) of reaction product of alkyl propylenediamine and L-glutamic acid ester in a molar ratio of 1:1 in the form of beige paste melting at 80 to 90° C. were left as the residue.

Example 1

Comparison Example C1 was repeated using 20 ppm of an aminosilicone (Magnasoft Ultra® FZ 3710, Union Carbide). 743 g (98% of the theoretical) of the reaction product in the form of a light yellow paste with a melting point of 75 to 80° C. were left as the residue.

Comparison Example C2

In a flask with a distillation bridge connected thereto, 125.9 g (0.5 mole) of dodecyl/tetradecyl propylenediamine and 73.6 g (0.5 mole) of L-glutamic acid were heated for 5 h to 175° C. (bottom) while nitrogen was passed over as an inert gas. At a bottom temperature of 135 to 145° C., most of the water expected during amide formation was distilled off with vigorous foaming. 182 g (95.8% of the theoretical) of reaction product of alkyl propylenediamine and L-glutamic acid ester in a molar ratio of 1:1 in the form of a beige paste with a melting point of 80 to 90° C. were left as residue.

Example 2

Comparison Example C2 was repeated using 10 ppm of the aminosilicone of Example 1. The elimination of water began at only 125° C. without any foaming. 9 ml of water were obtained as distillate after only 4 h and at a final temperature of 150° C. 187 g (98% of the theoretical) of reaction product in the form of a white paste were left as residue.

Comparison Example C3

In a 250 ml flask, a mixture of 25.1 g (0.1 mole) of dodecyl/tetradecyl propylenediamine, 14.7 g (0.1 mole) of L-glutamic acid and 100 ml of i-amyl alcohol as solvent and entraining agent was refluxed with stirring under nitrogen for about 2 h on a water separator until almost the calculated quantity of water had separated. The bottom temperature was at most 146° C. Most of the i-amyl alcohol was then distilled off in a water jet vacuum and the rest in an oil pump vacuum (1 h each). 36.1 g (95% of the theoretical) of reaction product in the form of a yellowish paste with a melting point of 72 to 82° C. were left as residue. The volume/time yield was 36.1 g/250 ml*4 h=0.036.

Example 3

In a 250 ml flask, a mixture of 75.3 g (0.3 mole) of dodecyl/tetradecyl propylenediamine, 44 g (0.3 mole) of L-glutamic acid and 5 mg of aminosilicone from Example 1 was heated with stirring for 3 h to 120–150° C. in the absence of entraining agent, the calculated quantity of water distilling off. 113 g (96% of the theoretical) of reaction product in the form of a light yellow paste with a melting point of 68 to 75° C. were left as residue. The volume/time yield was 113 g/250 ml*3h=0.15 and was therefore considerably higher than in Comparison Example C3.

Comparison Example C4

In a 1-liter glass flask with condenser, 124 g of butyl diglycol and 108 g of dodecyl/tetradecyl propylenediamine were heated under nitrogen to 90° C. 122 g of L-glutamic acid were stirred in and the mixture was heated for 2 h to 145° C. At 125° C., the reaction mixture began to foam vigorously as water started to separate. The progress of the reaction was monitored by conductivity measurement and the reaction was terminated by rapid cooling on reaching 2.2 mS/cm (5% by weight solution in water, 20° C.). 18 g of distillate accumulated. Another 175 g of water were added at 80° C. in order to obtain a 50% by weight solution of active substance. According to HPLC analysis, the product contained 19.5% by weight of butyl diglycol and 48.8 g of active substance. The Höppler viscosity at 20° C. measured 800 mPas. The product gelled in 3 days, had to be melted at 60° C. and then had a viscosity of 900 mPas.

Example 4

Comparison Example C4 was repeated, except that 15 ppm of the aminosilicone from Example 1 was added right at the beginning of the reaction. The removal of water was not accompanied by foaming. Only 15.8 g of distillate were obtained. According to HPLC analysis, the product contained 20.2% by weight of butyl diglycol and 49.7 g of active substance. It had a Höppler viscosity at 20° C. of 300 mPas. After three days, the product had a substantially constant viscosity and remained flowable and pumpable.

Example 5

Disinfection solutions with the following composition were prepared for color comparison:

20% by weight active substance of Examples 1 to 4, Comparison Examples C1 to C4.

10% by weight nonylphenol+10EO,

40% by weight ethanol and

30% by weight water.

The test solutions were examined in a Lange LICO 100 photometer (Hazen color scale). A reference solution in which the active substances were replaced by the same quantity by weight of glyoxal showed an APHA color of 5. The results are set out in Table 1:

TABLE 1

| | Color tests | | | | | | | |
| --- | --- | --- | --- | --- | --- | --- | --- | --- |
| | Ex. | | | | | | | |
| | 1 | 2 | 3 | 4 | C1 | C2 | C3 | C4 |
| APHA | 30 | 40 | 20 | 5 | 120 | 100 | 140 | 50 |

Example 6

The active substance concentrates of Examples 1 to 4 and Comparison Examples C1 to C4 were subjected to a storage test in a test formulation consisting of 25% by weight active substance
60% by weight demineralized water
10% by weight phenoxyethanol and
5% by weight coconut alcohol +10 butyl ether.

The results are set out in Table 2.

TABLE 2

| | Storage tests | | |
| --- | --- | --- | --- |
| | Storage Period | | |
| Examples | 14 Days | 1 Month | 3 Months |
| C1 | Clear | Cloudy | Flocculated |
| 1 | Clear | Clear | Clear |
| C2 | Clear | Very cloudy | Flocculated |
| 2 | Clear | Clear | Clear |
| C3 | Clear | Clear | Slight cloudy |
| 3 | Clear | Clear | Clear |
| C4 | Clear | Clear | Very cloudy |
| 4 | Clear | Clear | Clear |

What is claimed is:

1. A process for producing a glucoprotamine, said process comprising:
   (a) providing an N-substituted propylenediamine;
   (b) providing a 2-aminoglutaric derivative; and
   (c) reacting the N-substituted propylenediamine with the 2-aminoglutaric derivative in the presence of an aminosilicone.

2. The process according to claim 1, wherein the N-substituted propylenediamine corresponds to the general formula (I):

$$R^1-NH-CH_2-CH_2-CH_2NH_2 \quad (I)$$

wherein $R^1$ represents a linear alkyl group having from about 6 to about 22 carbon atoms.

3. The process according to claim 1, wherein the 2-aminoglutaric derivative corresponds to the general formula (II):

$$R^2OOC-CH_2CH_2CH(NH_2)COOH \quad (II)$$

wherein $R^2$ represents a hydrogen atom or an alkyl group having from about 1 to about 4 carbon atoms.

4. The process according to claim 1, wherein the N-substituted propylenediamine corresponds to the general formula (I):

$$R^1-NH-CH_2-CH_2-CH_2NH_2 \quad (I)$$

wherein $R^1$ represents a linear alkyl group having from about 6 to about 22 carbon atoms, and wherein the 2-aminoglutaric derivative corresponds to the general formula (II):

$$R^2OOC-CH_2CH_2CH(NH_2)COOH \quad (II)$$

wherein $R^2$ represents a hydrogen atom or an alkyl group having from about 1 to about 4 carbon atoms.

5. The process according to claim 1, wherein the N-substituted propylenediamine and the 2-aminoglutaric derivative are present in a molar ratio of from about 1:1 to about 1:2.

6. The process according to claim 4, wherein the N-substituted propylenediamine and the 2-aminoglutaric derivative are present in a molar ratio of from about 1:1 to about 1:2.

7. The process according to claim 1, wherein step (c) is carried out at temperatures of from about 60 to about 175° C.

8. The process according to claim 5, wherein step (c) is carried out at temperatures of from about 60 to about 175° C.

9. The process according to claim 6, wherein step (c) is carried out at temperatures of from about 60 to about 175° C.

10. The process according to claim 1, wherein the aminosilicone comprises from about 50 to about 2000 monomer units of the general formulae (IIIa) and (IIIb):

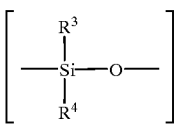

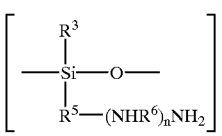

wherein $R^3$ and $R^4$ each independently represent an alkyl group having from about 1 to about 8 carbon atoms, $R^5$ and $R^6$ each independently represent an alkylene or hydroxy-substituted alkylene group having from about 1 to about 8 carbon atoms, and n is an integer of from about 1 to about 3.

11. The process according to claim 4, wherein the aminosilicone comprises from about 50 to about 2000 monomer units of the general formulae (IIIa) and (IIIb):

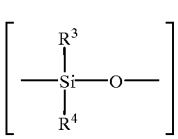

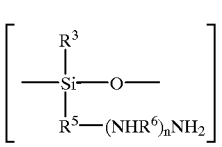

wherein $R^3$ and $R^4$ each independently represent an alkyl group having from about 1 to about 8 carbon atoms, $R^5$ and $R^6$ each independently represent an alkylene or hydroxy-substituted alkylene group having from about 1 to about 8 carbon atoms, and n is an integer of from about 1 to about 3.

12. The process according to claim 10, wherein $R^3$ and $R^4$ each represent a methyl group.

13. The process according to claim 10, wherein the amino silicone has a nitrogen content of from about 0.1 to about 5% by weight.

14. The process according to claim 11, wherein the amino silicone has a nitrogen content of from about 0.1 to about 5% by weight.

15. The process according to claim 1, wherein the aminosilicone is present in a foam reduction effective amount.

16. The process according to claim 4, wherein the aminosilicone is present in a foam reduction effective amount.

17. The process according to claim 6, wherein the aminosilicone is present in a foam reduction effective amount.

18. A color-stable and storage-stable glucoprotamine prepared by reacting an N-substituted propylenediamine with a 2-aminoglutaric derivative in the presence of an aminosilicone.

19. A color-stable and storage-stable glucoprotamine prepared by the process according to claim 9.

20. A color-stable and storage-stable glucoprotamine prepared by the process according to claim 14.

21. A method of stabilizing and reducing foam generation in a condensation reaction of an N-substituted propylenediamine and a 2-aminoglutaric derivative, said method comprising performing the condensation reaction in the presence of an aminosilicone.

* * * * *